United States Patent [19]

Cummings et al.

[11] Patent Number: 4,952,370
[45] Date of Patent: Aug. 28, 1990

[54] HYDROGEN PEROXIDE STERILIZATION METHOD

[75] Inventors: Arthur L. Cummings, Ponca City, Okla.; Robert W. Childers, Erie, Pa.

[73] Assignee: American Sterilizer Company, Erie, Pa.

[21] Appl. No.: 191,310

[22] Filed: May 6, 1988

[51] Int. Cl.$^5$ .............................. A61L 2/18; A61L 2/20
[52] U.S. Cl. ........................................ 422/28; 422/27; 422/292
[58] Field of Search .................... 422/28, 292, 27; 514/840; 424/616

[56] References Cited

U.S. PATENT DOCUMENTS

| | | | |
|---|---|---|---|
| Re. 32,672 | 5/1988 | Huth et al. | 514/840 X |
| 3,904,361 | 9/1975 | Egger | 422/27 |
| 4,169,123 | 9/1979 | Moore et al. | 422/28 X |
| 4,169,124 | 9/1979 | Forstrom et al. | 422/28 X |
| 4,225,556 | 9/1980 | Löthman et al. | 422/28 |
| 4,512,951 | 4/1985 | Koubek | 422/33 |
| 4,631,173 | 12/1986 | Müller et al. | 422/28 |

Primary Examiner—Barry S. Richman
Assistant Examiner—Jill Johnston
Attorney, Agent, or Firm—Kirkpatrick & Lockhart

[57] ABSTRACT

This process sterilizes the surfaces within a chamber wherein a first portion of the surfaces is at a temperature below 10° C. and a second portion of the surfaces is at a temperature greater than 20° C. The process includes the steps of introducing vapor phase hydrogen peroxide to the chamber, contacting the first portion with the vapor to effect condensation thereon, contacting the second portion with the vapor, applying a source of vacuum to the chamber and continuing to introduce vapor phase hydrogen peroxide into the chamber until the surfaces are sterile while preserving the temperature ranges of the first and second portions.

10 Claims, 2 Drawing Sheets

HYDROGEN PEROXIDE STERILIZATION METHOD

BACKGROUND OF THE INVENTION

1. Field of the Invention

The present invention relates to sterilization processes and more particularly, to hydrogen peroxide sterilization processes.

2. Description of the Prior Art

In equipment where potentially infectious specimens are processed and stored, contamination of the interior surfaces of the equipment and of the contents kept there due to spills and breakage of the specimens is an unfortunate but all too frequent occurrence. Removing the contaminated equipment from a busy laboratory for sterilization is often out of the question. Occasional manual cleaning with surface disinfectants has heretofore been the only practical solution. Another, less practical method of disinfecting, at least for smaller equipment, is to immerse it in glutaraldehyde. In some instances, contamination is so extensive that the equipment is discarded entirely and new equipment purchased to replace it.

Complete, in place sterilization of some laboratory equipment has not been possible, particularly in those items of equipment such as cold centrifuges and refrigerators having very cold interior surfaces or two or more zones of surfaces having widely differing temperatures. For example, some centrifuges maintain specimens at temperatures below 10° C. Other areas within the same centrifuge may be at room temperature.

Hydrogen peroxide in liquid form has long been recognized as a disinfectant. Koubek U.S. Pat. No. 4,512,951 describes a method of sterilization with liquid hydrogen peroxide which includes vaporizing an aqueous solution of hydrogen peroxide and passing the resulting hydrogen peroxide-water vapor mixture into an evacuated sterilization chamber where, upon contact with items to be sterilized, the vapor condenses to form a layer of liquid hydrogen peroxide on the items. The items to be sterilized are maintained at a temperature below the dewpoint of the hydrogen peroxide-water mixture to assure condensation, but the overall chamber temperature must be high enough to prevent condensation of the incoming vapor before it reaches the items. Following a suitable time for sterilization, the condensate is revaporized by passing filtered, preferably heated air over the surface of the items. The Koubek process is useful for sterilizing the cool items in the chamber but does not sterilize the warmer surfaces of the chamber itself.

Similar methods of applying a film of liquid hydrogen peroxide over an area to be sterilized and vaporizing the film by flowing heated air over the area are disclosed in Egger U.S. Pat. No. 3,904,361 and Lothman et al. U.S. Pat. No. 4,225,556.

Sterilization with gaseous hydrogen peroxide is described by Moore et al. U.S. Pat. No. 4,169,123 and Forstrom et al. U.S. Pat. No. 4,169,124. The methods described in those two patents involve surrounding an article to be sterilized with vapor phase hydrogen peroxide and maintaining contact between the article and the sterilant at temperatures below 80° C. until sterility is achieved. The lowest temperature disclosed in either the Moore or Forstrom patents is 20° C. The vapor phase hydrogen peroxide is removed from the chamber following the sterilization cycle by evacuation. A uniform temperature throughout the sterilization chamber is contemplated by the methods of the Moore and Forstrom patents.

While the prior art methods of sterilization with hydrogen peroxide are useful in some environments, they do not contemplate environments such as a cold centrifuge or refrigeration equipment which have two or more zones of widely differing temperature ranges within the same piece of equipment. In these environments, where potentially contaminating specimens are processed or stored, spills routinely occur. In the centrifuge, airborne contamination is common. It would be desirable to sterilize the interior of the equipment before having to open it to remove the contents to spare the technician the risk of exposure to contamination. It would also be desirable to sterilize without altering the temperatures within the equipment to maintain specimens at the desired temperature.

There was, prior to the present invention, no convenient method for sterilizing equipment having two or more zones of widely differing temperature ranges within the same chamber without substantially altering those temperature ranges. The known hydrogen peroxide sterilization methods either heat cool surfaces to revaporize liquid sterilant for removal, as in the Koubek patent, or contemplate a uniform temperature throughout the chamber, as in the Moore and Forstrom patents.

It is an object of the present invention to provide a process for sterilizing surfaces within equipment, such as cold centrifuges or refrigerators, having very cold portions without significantly elevating the temperature of the cold portion of the surfaces. It is a further object of the present invention, to provide such a process where two or more surface portions in the same chamber, each having widely differing temperature ranges, can be simultaneously sterilized without significantly altering the temperature of any surface portion.

SUMMARY OF THE INVENTION

The present invention provides a process for sterilizing surfaces within a chamber wherein a portion of the surfaces are at a temperature below 10° C. The process includes the steps of introducing vapor phase hydrogen peroxide into the chamber, contacting such portion of the surfaces with the vapor to effect condensation of the vapor on that portion, applying a source of vacuum to the chamber and continuing to introduce vapor phase hydrogen peroxide into the chamber until the surfaces are sterile while preserving the temperature of such portion of the surface. The sterilant condensate is concentrated while on such portion of the surfaces.

The process of the present invention is also useful for sterilizing the surfaces within a chamber wherein, in addition to the first portion having a temperature below 10° C, there is a second portion of the surfaces at a temperature greater than 20° C. To accommodate the "warmer" portion, the process also includes the step of contacting the second portion of the surfaces with vapor phase hydrogen peroxide. The vapor phase hydrogen peroxide is continued to be introduced into the chamber until the surfaces are sterile while preserving the temperature ranges of both the first and the second portions of the surfaces.

BRIEF DESCRIPTION OF THE DRAWINGS

The present invention can be better understood by reference to the Figures in which.

DETAILED DESCRIPTION OF THE PREFERRED EMBODIMENTS

Figure 1:
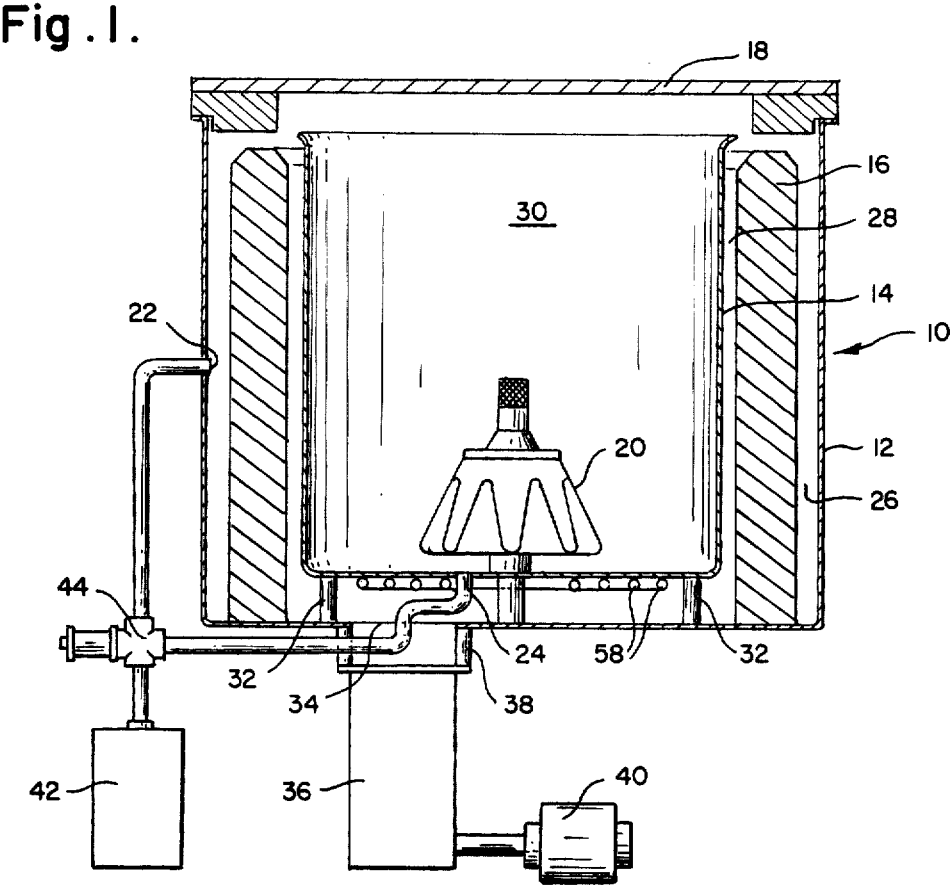
FIG. 1 illustrates a centrifuge having first and second portions on its interior surfaces in which the process of the present invention can be practiced.

The process of the present invention can be practiced in any "cold" environment where it is desirable to preserve the temperature of the cold surfaces. "Cold" as used herein shall mean a temperature at or below about 10° C. Significantly, the process of the present invention can also be used in an environment having interior surfaces, portions of which are cold and portions of which are warmer without significantly altering the temperature of the different portions. "Warm" as used herein shall mean temperatures at or greater than about 20° C.

Sterilization techniques for use on cold surfaces where it is important to maintain the cold temperature have not been previously available. It has been discovered that there is a relationship between sterilization time and hydrogen peroxide vapor concentration. At low temperatures, the concentration of the vapor decreases so that the time required for complete sterilization increases. In order to reduce the time required for complete sterilization, the preferred embodiment of the process of the present invention employs a modification of the technique of condensing the hydrogen peroxide vapor on the cold portions of the interior surfaces in conjunction with the vapor phase hydrogen peroxide sterilization of the warm portions of the interior surfaces to sterilize across a variety of temperature gradients within a short period of time. It is believed that sterilization of the cold surfaces occurs ultimately by means of a combination of contact with liquid and vapor phase hydrogen peroxide.

The condensed sterilant is also concentrated while on the cold surface to enhance the sterilants' effectiveness. The hydrogen peroxide vapor introduced into the chamber is in actual practice a binary mixture of hydrogen peroxide and water vapors. When the vapors condense, a liquid film of water and hydrogen peroxide coats the cold surface. Water is more volatile than hydrogen peroxide so it will evaporate first. To take advantage of the different volatilities of water and hydrogen peroxide and thereby selectively revaporize the water to concentrate the hydrogen peroxide condensate, a source of vacuum is applied to the chamber to evaporate the water. Eventually the hydrogen peroxide condensate is evaporated also.

Following the initial introduction of vapor phase hydrogen peroxide into the chamber and the condensation of such vapor on the cold surfaces, in addition to the application of vacuum to the chamber, the injections of vapor phase hydrogen peroxide continue, thereby establishing a flow through system. One advantage to such a system is that the absolute chamber pressure can be maintained above the vapor pressure of hydrogen peroxide and below the vapor pressure of water at the relevant temperature to control the evaporation of the condensate. The water, as stated above, will evaporate under these conditions. The hydrogen peroxide will not evaporate as readily, leaving a condensate of very concentrated hydrogen peroxide on the cold surfaces.

Hydrogen peroxide is known, however, to degrade into water and oxygen. Thus, the concentration of hydrogen peroxide in the condensate and in the vapor phase decreases over time. As the hydrogen peroxide degrades, the resulting water in the condensate evaporates and, to an extent, further concentrates the remaining hydrogen peroxide condensate. The quantity of remaining condensate, however, in time, will not be sufficient to completely sterilize the surfaces. Similarly, as degradation progresses, the remaining vapor phase hydrogen peroxide may be insufficient to sterilize some areas of the chamber. To compensate for the degradation of the hydrogen peroxide and thereby maintain the desired concentration of vapor phase hydrogen peroxide and liquid hydrogen peroxide in the condensate, additional injections of vapor phase hydrogen peroxide are provided. The continued vacuum removes much of the water vapor to avoid a build up of water vapor in the chamber.

As an example of the foregoing, at 10° C., the vapor pressure of water is 9.2 mm Hg. At 10° C., in an environment of 100% hydrogen peroxide, the vapor pressure of hydrogen peroxide is 0.642 mm Hg. To revaporize the water without revaporizing the hydrogen peroxide in the binary condensate, the absolute chamber pressure should be maintained at a level above 0.642 mm Hg. but below 9.2 mm. Hg. By using standard saturated steam tables and standard tables for "Total Vapor Pressure of Hydrogen Peroxide-Water Solution" and "Vapor Composition (Mole Fraction H ) Over Hydrogen Peroxide-Water Solutions" such as those reproduced in Perkins, PRINCIPALS AND METHODS OF STERILIZATION IN HEALTH SCIENCES (2d ed. 1976) and W. C. Schumb, et al., HYDROGEN PEROXIDE, pp. 221–227 (Reinhold pub. 1955), respectively, and hereby incorporated herein by reference, the relevant vapor pressures can be determined for any temperature. If a 30% hydrogen peroxide vapor is injected into the chamber, it can be determined based on the tables reprinted in Schumb supra., that at 10° C., the condensate formed due to the evaporation of the water component of the mixture will be slightly less than about 75% hydrogen peroxide. The remaining vapor therefore, is no longer 30% hydrogen peroxide because the water vapor portion has been increased. As degradation occurs, the hydrogen peroxide component in the vapor decreases further. The continued injections of vapor phase hydrogen peroxide coupled with the continuous pull of vacuum in the chamber provides a flow through system which replaces the hydrogen peroxide to overcome the effects of degradation and maintain the desired vapor phase hydrogen peroxide concentration for sterilization of the warm surfaces. It also replenishes the condensate on the cold surfaces and promotes the concentration of the liquid hydrogen peroxide to enhance sterilization of the cold surfaces. The absolute chamber pressure and sterilant concentrations are thus maintained in a steady state condition.

By using vacuum to evaporate the condensate, unlike the streams of filtered warm air used for evaporation by prior art techniques, the temperature of the cold surfaces is not significantly altered. The introduction of warm air into a spinning centrifuge, for example, would raise the temperature about 10–20° C. In very high speed centrifuges, the introduction of air could cause considerable damage to the spinning rotor.

While those skilled in the art will recognize that there may be a variety of environments which have such cold and warm portions, the process of the present invention will be described as it is used in a cold ultracentrifuge.

Referring to FIG. 1, the ultracentrifuge 10 includes an outer shell 12 and a lid 18 which define therein a chamber 30. The ultracentrifuge 10 also includes an inner tub 14, an armor plated insulating layer 16 and a rotor 20. Posts 32 elevate tub 14 above the bottom of the chamber. An outer gap 26 is defined between the outer shell 12 and the insulating layer 16 and an inner gap 28 is defined between the insulating layer 16 and the inner tub 14. Side inlet port 22 and bottom inlet port 24 are provided for the introduction of vapor phase hydrogen peroxide.

A vacuum port 34 is provided in the floor of shell 12. A diffusion pump 36, which may be of any suitable known variety, is separated from the exterior bottom of shell 12 by a spacer 38. A vacuum pump 40 of any suitable known variety is connected via the converter portion of vaporizer/converter 42 by standard piping to the diffusion pump 36. The bottom inlet port 24 passes through vacuum port 34.

Figure 2:
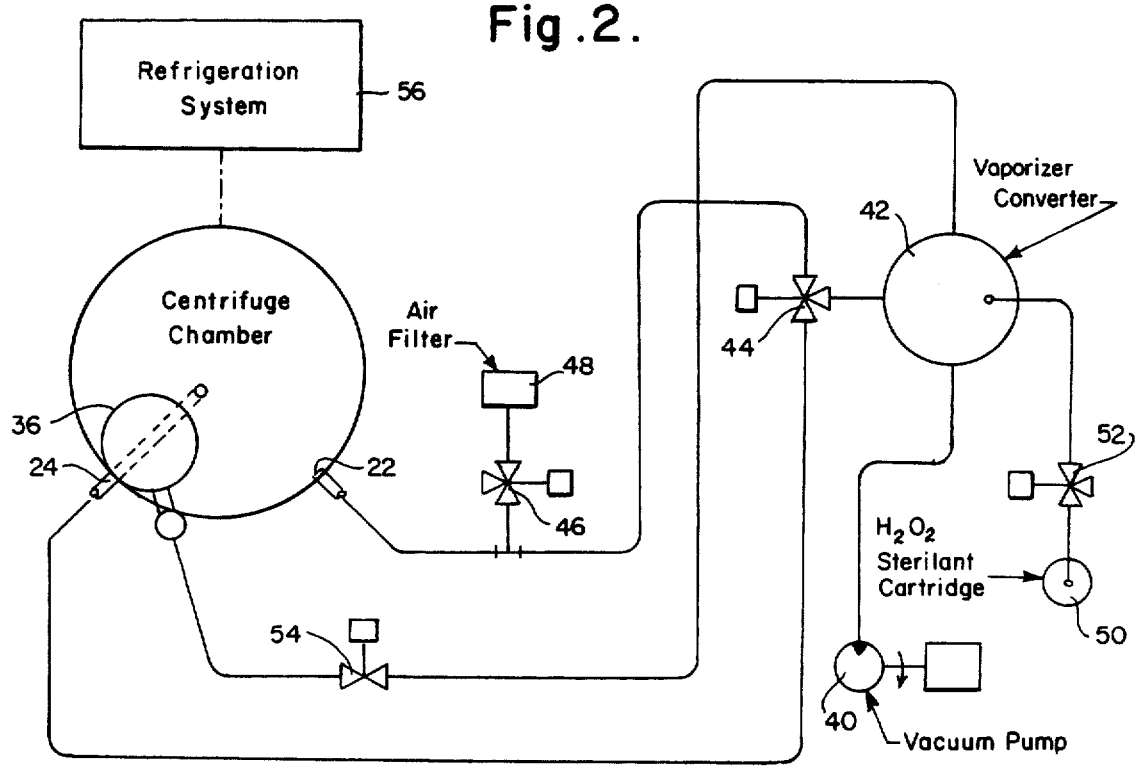
FIG. 2 is a schematic diagram of the centrifuge of FIG. 1.

Referring to FIG. 2, a vaporizer/converter 42 is connected by suitable known piping to inlet ports 22 and 24. A three-way diverter valve 44 controls the direction of vapor flow from vaporizer 42 to one of the two inlet ports 22 or 24. An air break solenoid valve 46, connected to air filter 48 is provided adjacent inlet port 22. A source of liquid hydrogen peroxide and water is provided by cartridge 50 and is injected at selected intervals into vaporizer 42 by injection solenoid valve 52.

A vacuum/exhaust solenoid valve 54 is positioned in the line from vacuum pump 40 to diffusion pump 36. A refrigeration system 56 of the kind typically found in cold centrifuges is also provided and suitably connected to centrifuge 10. Refrigeration coils 58 are provided beneath the floor of tub 14 in gap 28. Suitable controls (not shown) are also provided.

The vaporizer/converter 42 is of the type described in copending application Serial No. 070,271 entitled "Flow-Through Vapor Phase Sterilization System", assigned to the assignee hereof. The vaporizer/converter 42 includes two chambers, one for vaporizing liquid hydrogen peroxide solutions and one for promoting the degradation of hydrogen peroxide vapor exhausted from a chamber into water and oxygen for discharge.

In a cold ultracentrifuge the temperature of the rotor 20 is about 4° C. The temperature of the floor of tub 14 is initially about −11° C., but, due to warmth created by the turbulence created by the spinning rotor and the injected vapor, the temperature rises to about 4 to 10° C. The chamber temperature in general is about 25° C. with the outer shell 12, the gap 26 and insulating layer 16 being the warmest. It is important to maintain the temperature of the rotor 20 at about 4° C. to keep any specimens held therein at the desired temperature.

Figure 3:
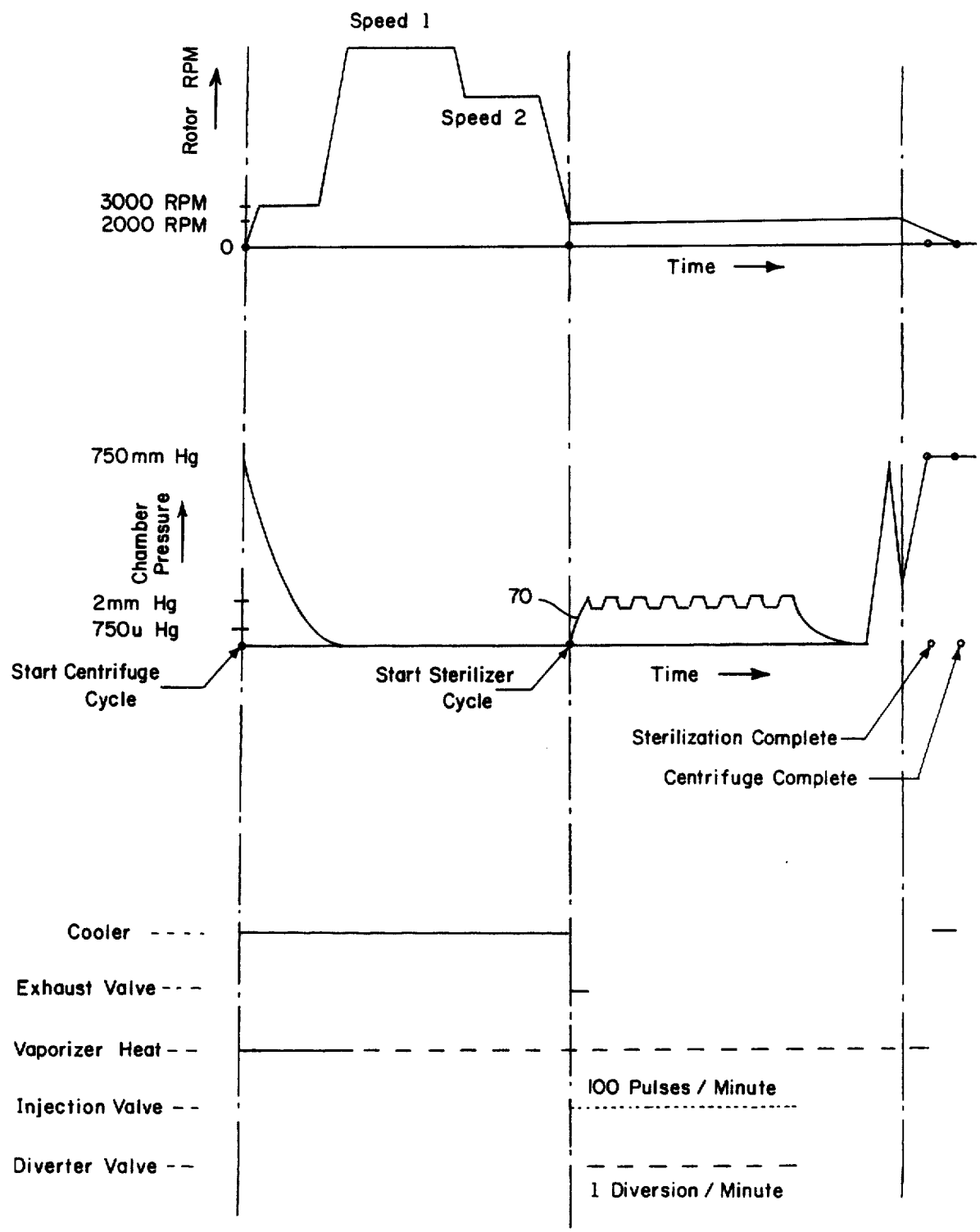
FIG. 3 is a graph illustrating a preferred embodiment of the sterilization process of the present invention as practiced in the centrifuge of FIG. 1.

The preferred embodiment of the process of the present invention as practiced in centrifuge 10 is shown in FIG. 3. FIG. 3 illustrates in the top graph, the rpms of the centrifuge rotor 20 during the centrifugation cycle and, in the middle graph, the simultaneous sterilization process. The status of the refrigeration controls, the exhaust valve 54, the vaporizer 42, the injection valve 52 and the diverter valve 44 are provided at the bottom of FIG. 3. A basic cycle useful in the centrifuge 10 includes the steps of initially pulling a vacuum in chamber 30. While the initial pull of vacuum is preferred, it is not required. In one embodiment of the process, the vacuum is pulled to less than about 300 microns (0.3 mm Hg). This step permits the temperatures throughout the centrifuge 10, particularly the cold surface temperatures of the tub, rotor and rotor contents, to stabilize. The initial vacuum also removes any water vapor present in chamber 30. As shown in FIG. 3, a centrifuge run may take place at this stage. When the desired vacuum level is achieved very rapid speeds are initiated. Occasionally, two levels of rapid speeds are run. Following completion of speed 2, the rpm of the rotor 20 is reduced to about 2000 and the sterilization phase of the cycle begins. The vacuum source is then preferably turned off temporarily by closing the vacuum/exhaust valve 54. Thereafter, vapor phase hydrogen peroxide is introduced into chamber 30 through side inlet port 22 for approximately one minute. This step is represented by the first peak 70 on the middle graph of FIG. 3. Condensation begins to occur on those portions of the surfaces within chamber 30 which are below 10° C. In embodiments where the initial pull of vacuum is terminated during the first vapor phase hydrogen peroxide injection, the pull of vacuum is resumed after the completion of the initial injection and preferably continues uninterrupted throughout the remainder of the process. If the initial vacuum pull is not terminated, more vapor may have to be injected initially. The pull of vacuum at about this point and at least intermittently thereafter is an important step of the process of the present invention. The vapor phase hydrogen peroxide injections also continue. At this stage the flow-through conditions discussed above begin to be established. As stated previously, the vacuum is maintained at a level sufficient to substantially evaporate the water component of the sterilant which will have condensed on the cold surfaces, thereby concentrating the hydrogen peroxide component. The desired vapor phase hydrogen peroxide concentration is maintained by the continued injections of vapor.

The introduction of vapor phase hydrogen peroxide is continued first by injections through bottom inlet port 24 for one minute, then by injections through side inlet port 22 for one minute. Injections of sterilant vapor at two sites facilitates distribution of sterilant throughout the chamber. The injections of sterilant vapor continue in such alternating fashion for a period of, for example, four, eight, sixteen or thirty-two minutes, depending upon the extent of the areas within centrifuge 10 that are to be sterilized. A short cycle will sterilize the areas within tub 14 where contamination from specimens is more likely to be concentrated. This cycle would typically be used on a routine basis. A longer cycle will also achieve sterilization of the outer gap 26 and interior surfaces of outer shell 12. This cycle would typically be used prior to servicing of the centrifuge 10 to provide a contamination free work area for service technicians. The continued introduction of vapor phase hydrogen peroxide and the continued application of vacuum assures continuing condensation and concentration of the hydrogen peroxide for sterilization of the cold portions, effective sterilization of the warm portions and revaporization of the condensate without altering the temperature ranges of the cold and warm portions.

Following the sterilization phase of the cycle during which the injections of sterilant vapor occur, the vacuum is pulled to reduce the absolute chamber pressure to a level below the vapor pressure of hydrogen peroxide at the cold portions of the surfaces to remove sterilant vapor from the chamber 30 and to evaporate any remaining condensate from the cold portions of the surfaces. The vacuum is turned off for a moment and filtered air is introduced to chamber 30 to dilute any remaining vapors. The vacuum is pulled again, though not as deeply. The vacuum is then turned off and the chamber is permitted to return to atmospheric pressure at the end of the centrifugation/sterilization run.

A series of tests were run using an ultracentrifuge 10 similar to that shown in FIG. 1.

Tests were run to establish the temperature ranges of various areas within the centrifuge before, during and after the centrifugation and sterilization runs. The results are set forth below:

| Area | Temp. range °C. |
| --- | --- |
| inner gap 28 | 19.5 to 23.6 |
| bottom of tub 14 | −11.2 to 17.7 |
| space just above bottom of tub 14 | −2.1 to 14.5 |
| inside wall of tub 14 | 5.0 to 20.3 |
| middle of rotor 20 | 4.0 to 7.2 |
| top of rotor 20 | 5.0 to 10.6 |
| bottom of rotor 20 | 4.1 to 6.5 |
| outer gap 26 | 27.3 to 27.7 |

In each series of tests discussed below, coupons inoculated with $10^6$ *Bacillus subtilis var. globioii* and $10^6$ *Bacillus stearothermoohilus* were placed in the centrifuge 10. One group of coupons of each bacterial type was coated with 20% fetal calf serum. A second group of coupons of each bacterial type was not coated with serum.

In the first series of tests, four groups of coupons were placed on the floor of tub 14. A vacuum was initially pulled in the chamber, then the vacuum source was turned off. The vapor phase hydrogen peroxide was injected and permitted to condense on the coupons. The total hydrogen peroxide injected was 0.7g. Filtered atmospheric air was then admitted into the chamber. No additional vacuum and no additional vapor phase hydrogen peroxide injections were applied to the chamber. Immediately following condensation of the vapor on the coupons, three groups of coupons were removed from the chamber under sterile conditions. One group remained in the chamber for three minutes, then was removed and assayed for sterility. One of the groups of coupons immediately removed from the chamber was assayed for sterility immediately. Two groups were placed in a refrigerator. While refrigerated, the temperature and sterility conditions were maintained. The condensate remained on the coupons. Of the groups of coupons which were refrigerated, one group was removed at 6 minutes and the other at 20 minutes and assayed for sterility. None of the four groups of coupons were sterile.

A second series of tests was run. The coupons were again placed on the floor of tub 14. Hydrogen peroxide vapor was injected into the chamber and condensate formed on the coupons. The total hydrogen peroxide injected was 0.65 g. After one minute exposure to the hydrogen peroxide condensate, the vacuum source was turned on for four minutes. No additional injections of hydrogen peroxide vapor were made. The coupons were then assayed for sterility. The coupons inoculated with *Bacillus stearothermoohilus*, both with and without serum, were sterile. The coupons inoculated with *Bacillus subtilus*, with and without serum, were not sterile.

Comparing the first and second series of tests, it is apparent that the results can be improved somewhat by the application of vacuum but not enough to sterilize all types of bacterial spores.

A third series of tests was run. Coupons were placed on the rotor and on the tub floor. An initial vacuum was pulled to below 300 microns. The vacuum source was turned off and vapor phase hydrogen peroxide was injected until the chamber pressure was increased by 1.5–2.0 mm Hg. Additional injections were made every twenty to thirty seconds for fifteen minutes. After the initial vacuum, no additional vacuum was pulled during the process. The results were as follows. In a first run, none of the bacillus subtilus coupons, whether on the floor or the rotor were sterile. The *Bacillus stearothermophilus* coupons which had been placed on the floor were not sterile. Those which had been placed on the rotor were sterile. In a second run all of the *Bacillus stearothermophilus* coupons were sterile, two out of four of the *Bacillus subtilus* coupons which had been placed on the rotor were sterile and three out of four *Bacillus subtilus* coupons which had been placed on the floor were sterile.

In a final series of tests, the conditions were the same as those in the second series, except that additional injections of vapor phase hydrogen peroxide were made during the four minute vacuum period. In this series, coupons of each bacterial type having four different levels of serum coating (5, 25, 50 and 100 microliters of 20% fetal calf serum) were placed on the tub floor. Coupons of each bacterial type without the serum coating were also placed on the tub floor. Six coupons of each bacterial type having 5, 25 and 50 microliters of serum coating and eight coupons of each bacterial type having 100 microliters serum were assayed for sterility and all were found to be sterile. All coupons of each bacterial type without serum were also found to be sterile.

Additional tests run using a centrifuge similar to that shown in FIG. 1 corroborate the test results. A 30% hydrogen peroxide solution was vaporized and injected into the centrifuge during a 4 minute (3 g hydrogen peroxide), 8 minute (5 g hydrogen peroxide) and 16 minute (10 g hydrogen peroxide) cycle during which vacuum was continuously pulled and additional vapor phase hydrogen peroxide injections were made. Each cycle was followed by a sixteen minute exhaust period. Coupons inoculated with $10^6$ *Bacillus subtilus var. globioii* spores were placed in the tub 14, the inner gap 28, and the outer gap 26. The coupons were assayed for sterility in Tryptic Soy Broth and incubated at 37° C. for seven days. The four minute cycle sterilized 118 out of 124 coupons in the tub 14, 107 out of 124 coupons in the inner gap 28 and 112 out of 124 coupons in the outer gap 26.

The eight minute cycle sterilized 120 out of 120 coupons in the tub 14, 118 out of 120 in the inner gap 28 and 116 out of 120 in the outer gap 26. In the sixteen minute cycle, of the 128 coupons placed in each location, only one coupon in the outer gap 26 was not sterilized.

These results demonstrate that, under the test conditions, a cycle of eight or more minutes can be used for routine decontamination of the centrifuge tub area and a cycle of sixteen or more minutes can be used to decontaminate the entire interior of the centrifuge prior to servicing or after evidence of a failure within the system.

It can be seen from a comparison of the results obtained in the foregoing tests that both the application of vacuum and the additional injections of hydrogen peroxide vapor throughout the sterilization phase of a cycle are necessary for achieving effective sterilization in a reasonable period of time in an environment with widely differing temperature zones. Moreover, it is apparent that the combination of techniques employed by the process of the present invention permits such sterilization while preserving the desired temperature ranges of cold and warm portions of the surfaces within a chamber. Surface portions between 10 and 20° C. are also sterilized principally by contact within the vapor phase hydrogen peroxide. Some condensation may occur on these portions.

What is claimed is:

1. A process for sterilizing surfaces within a chamber, a portion of said surfaces being maintained at a temperature below about 10° C., comprising the steps of:
    introducing vapor phase hydrogen peroxide at a temperature above about 10° into said chamber;
    contacting said portion of said surfaces with said vapor phase hydrogen peroxide to effect condensation of said vapor phase hydrogen peroxide on said portion;
    applying a source of vacuum to said chamber; and
    continuing to introduce vapor phase hydrogen peroxide into said chamber until said surfaces are sterile while preserving said temperature of said portion of said surfaces below about 10° C.

2. The process recited in claim 1 further comprising the step of evacuating said chamber prior to the initial introduction of vapor phase hydrogen peroxide into said chamber.

3. The process recited in claim 1 wherein the vacuum is drawn to maintain the absolute vapor pressure of the chamber at a level above the vapor pressure of hydrogen peroxide and below the vapor pressure of water at the temperature of said portion of said surface.

4. The process recited in claim 3 further comprising the step of drawing the vacuum after sterility of said surfaces is achieved to lower the absolute pressure of the chamber to another level below the vapor pressure of hydrogen peroxide at the temperature of said portion of said surfaces.

5. The process recited in claim 1 wherein said continuing introduction of vapor phase hydrogen peroxide into said chamber is through at least two locations to facilitate distribution of said vapor phase hydrogen peroxide within said chamber.

6. A process for sterilizing surfaces within a chamber, a first portion of said surfaces being maintained at a first temperature below about 10° C. and a second portion of said surfaces being at a second temperature greater than about 20° C., comprising the steps of:
    introducing vapor phase hydrogen peroxide at a temperature above about 10° C. into said chamber;
    contacting said first portion of said surfaces with said vapor phase hydrogen peroxide to effect condensation of said vapor phase hydrogen peroxide on said first portion;
    contacting said second portion of said surfaces with vapor phase hydrogen peroxide;
    applying a source of vacuum to said chamber; and
    continuing to introduce vapor phase hydrogen peroxide into said chamber until said surfaces are sterile while preserving said first temperature of said first portion of said surfaces below about 10° C. and said second temperature of said second portion of said surfaces greater than about 20° C.

7. The process recited in claim 6 further comprising the step of evacuating said chamber prior to the initial introduction of vapor phase hydrogen peroxide into said chamber.

8. The process recited in claim 6 wherein the vacuum is drawn to maintain the absolute vapor pressure of the chamber at a level above the vapor pressure of hydrogen peroxide and below the vapor pressure of water at the temperature of said first portion.

9. The process recited in claim 8 further comprising the step of drawing the vacuum after sterility of said surfaces is achieved to lower the absolute vapor pressure of the chamber to another level below the vapor pressure of hydrogen peroxide at the temperature of said first portion.

10. The process recited in claim 6 wherein the application of said source of vacuum to said chamber is continued throughout said process.

* * * * *

UNITED STATES PATENT AND TRADEMARK OFFICE
CERTIFICATE OF CORRECTION

PATENT NO. : 4,952,370

DATED : August 28, 1990

INVENTOR(S) : Arthur L. Cummings and Robert W. Childers

It is certified that error appears in the above-identified patent and that said Letters Patent is hereby corrected as shown below:

Col. 4, line 30, delete "H)" and substitute therefor $--H_2O_2)--$.

Col. 7, line 26, delete "globioii" and substitute therefor --globigii--.

Col. 8, line 46 and 47, delete "globioii" and substitute therefor --globigii--.

Col. 8, line 54, after "120", second occurrence, add a space.

Col. 9, line 37, delete "surface" and substitute therefor --surfaces--.

Signed and Sealed this

Twenty-first Day of April, 1992

Attest:

HARRY F. MANBECK, JR.

*Attesting Officer*      *Commissioner of Patents and Trademarks*